United States Patent [19]
Li

[11] Patent Number: 6,090,996
[45] Date of Patent: Jul. 18, 2000

[54] IMPLANT MATRIX

[75] Inventor: Shu-Tung Li, Oakland, N.J.

[73] Assignee: Collagen Matrix, Inc., Franklin Lakes, N.J.

[21] Appl. No.: 08/906,180

[22] Filed: Aug. 4, 1997

[51] Int. Cl.[7] .................................................. A61F 2/02
[52] U.S. Cl. ........................... 623/11; 623/12; 623/13; 606/151; 606/154; 606/213
[58] Field of Search .................... 606/151, 213, 606/108, 153, 154, 155, 228, 229, 230; 623/1, 11, 12, 13, 66; 602/41–43, 48, 53

[56] References Cited

U.S. PATENT DOCUMENTS

| | | | |
|---|---|---|---|
| 3,157,524 | 11/1964 | Artandi | 106/122 |
| 3,272,204 | 9/1966 | Artandi et al. | 623/1 |
| 3,520,402 | 7/1970 | Nichols et al. | 206/59 |
| 4,193,813 | 3/1980 | Chvapil | 106/122 |
| 5,116,357 | 5/1992 | Eberbach | 606/151 |
| 5,147,374 | 9/1992 | Fernandez | 606/151 |
| 5,282,847 | 2/1994 | Trescony et al. | 623/1 |
| 5,282,856 | 2/1994 | Ledergerber | 623/8 |
| 5,310,407 | 5/1994 | Casale | 604/51 |
| 5,326,350 | 7/1994 | Li | 623/11 |
| 5,334,216 | 8/1994 | Vidal et al. | 606/213 |
| 5,376,376 | 12/1994 | Li | 424/443 |
| 5,458,636 | 10/1995 | Brancato | 606/151 |
| 5,514,181 | 5/1996 | Light et al. | 623/12 |
| 5,593,417 | 1/1997 | Rhodes | 623/1 |
| 5,697,978 | 12/1997 | Srgo | 606/151 |

OTHER PUBLICATIONS

Miller et al., "Preparation and Characterization of the Different Types of Collagen," Methods in Enzymology, vol. 82 (1982).

Oneson et al., "The Preparation of Highly Purified Insoluble Collagens," The Journal of the American Leather Chemists Association, vol. LXV, No. 9 (Sep. 1970).

*Primary Examiner*—Mickey Yu
*Assistant Examiner*—Tram A. Nguyen
*Attorney, Agent, or Firm*—Fish & Richardson P.C.

[57] ABSTRACT

An implant which includes a porous matrix sheet made of a biopolymeric material which is biocompatible and bioresorbable. The porous matrix sheet has at least one portion spaced from and overlapping another portion of the matrix sheet, and has a density ranging from about 0.05 g/cm$^3$ to about 1.3 g/cm$^3$, a pore size ranging from about 0.1 $\mu$m to about 1,500 $\mu$m, and a spacing between overlapping portions of the matrix sheet ranging from about 0.1 $\mu$m to about 2,000 $\mu$m.

26 Claims, 3 Drawing Sheets

IMPLANT MATRIX

BACKGROUND OF THE INVENTION

During certain surgical procedures, such as a biopsy of an organ, a wound void is created by excised tissue taken as part of the operation. In these operations, it is preferred or necessary that a biopolymeric implant be placed in the void to facilitate healing. In other medical procedures, a biopolymeric material is placed on or near the external surface of a body fluid vessel, such as injecting at the bladder neck a collagen paste-like material to cause coaptation of the bladder neck tissue so as to improve continence.

SUMMARY OF THE INVENTION

The present invention features an implant for placement in a body. The implant includes a porous matrix sheet, made of biocompatible and bioresorbable biopolymeric material, which has at least one portion spaced from and overlapping another portion of the matrix sheet, and has a density ranging from about 0.05 g/cm$^3$ to about 1.3 g/cm$^3$, a pore size ranging from about 0.1 μm to about 1,500 μm, and a spacing between overlapping portions of the matrix sheet ranging from about 0.1 μm to about 2,000 μm.

Suitable biopolymeric materials, which can be either natural or synthetic, include but are not limited to collagen, elastin, fibrin, polysaccharide, or a combination thereof. The dimensions of the density, pore size, and spacing between two overlapping and separate portions of the implant set forth herein are determined in a dry state. The dryness can be easily achieved by air drying in a hood overnight, or by any other methods, e.g., freeze-drying, which bring about the same or similar state of dryness. Both the pore size and spacing are determined by scanning electron micrograph or by any other analogous or suitable method. The pore size is defined as the longest distance across an open pore, the spacing is defined as the shortest distance between two overlapping and apart portions, and the volume expansion rate is defined as the ratio of the volume (cm$^3$) of the implant in a fully hydrated and maximally expanded state to the volume (cm$^3$) of the implant in a dry state.

One or more of the following features may also be included: The implant, upon absorption of a fluid (e.g., water or a body fluid such as blood), can be expandable and have a volume expansion rate ranging from about 2 cm$^3$/cm$^3$ to about 100 cm$^3$/cm$^3$ (preferably, from about 4 cm$^3$/cm$^3$ to about 80 cm$^3$/cm$^3$), and, upon expansion, can have a density ranging from about 0.01 g/cm$^3$ to about 0.5 g/cm$^3$, a pore size ranging from about 10 μm to about 2,000 μm, and a spacing between overlapping portions of the matrix sheet ranging from about 10 μm to about 5,000 μm. The implant can be radially, longitudinally, or both directions, expandable upon absorption of a fluid, in which the longitudinal direction is along a defined axis of symmetry of the implant and the radial direction is perpendicular to the longitudinal direction. The matrix sheet may be folded into any general shape. An implant generally shaped as a cylinder or a parallelepiped can be obtained by folding the matrix sheet either spirally or sinusoidally.

Cellular growth in the spacing between overlapping and separate portions of the matrix sheet hastens wound healing. Other features and advantages of the implant of this invention will be apparent from the following drawings, detailed description, and claims.

DESCRIPTION OF THE PREFERRED EMBODIMENTS

A preferred embodiment of this invention is a wound-healing implant matrix having a geometrically and directionally controlled expanding properties, thereby allowing the matrix to be delivered in a compact form to an affected wound site in the body via a delivery device such that upon deployment and when in contact with body fluid, the matrix expands in a geometrically and directionally controllable manner to facilitate the wound healing and augment the tissue function. Depending on the particular clinical application, the geometry and direction of expansion of the matrix may be of significant importance. For example, in some surgical or diagnostic applications, expansion of a folded spiral matrix into a more open spiral matrix with a concurrent increase in total volume is of considerable advantages over the conventional matrices. The spiral opening of the structure upon expansion facilitates cellular ingrowth and hasten wound healing. In addition, the spiral opening of the structure upon expansion allows the material to occupy a maximum space with a minimum delivery volume. In general, controlling the direction and geometry of expansion of the matrix will optimize the desired function of the matrix in vivo.

Figure 1:
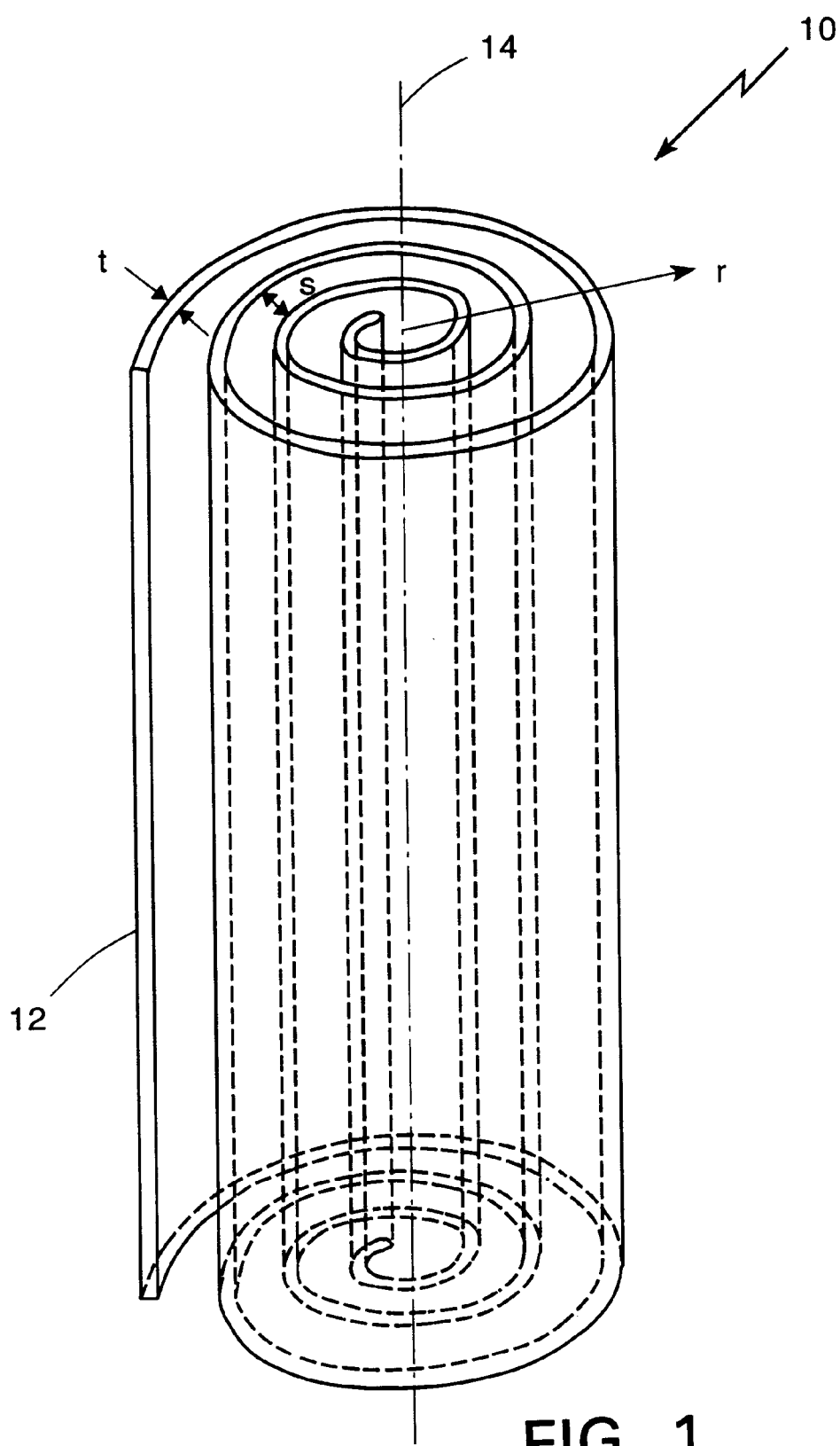
FIG. 1 is a perspective view of a spirally rolled implant, shown partially in dash lines.
Figure 2:
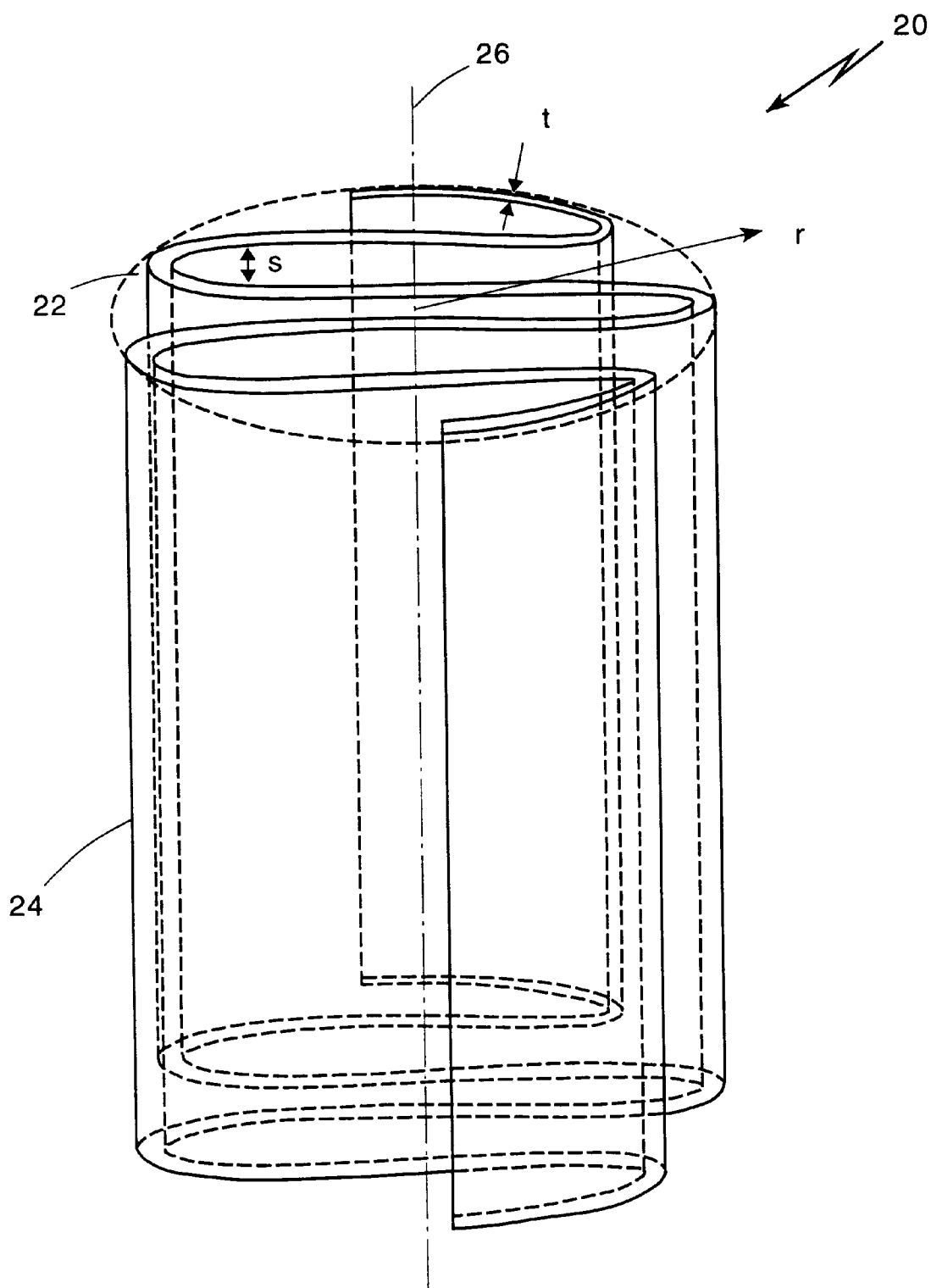
FIG. 2 is a perspective view of a sinusoidally folded implant having a generally cylindrical shape, shown partially in dash lines.
Figure 3:
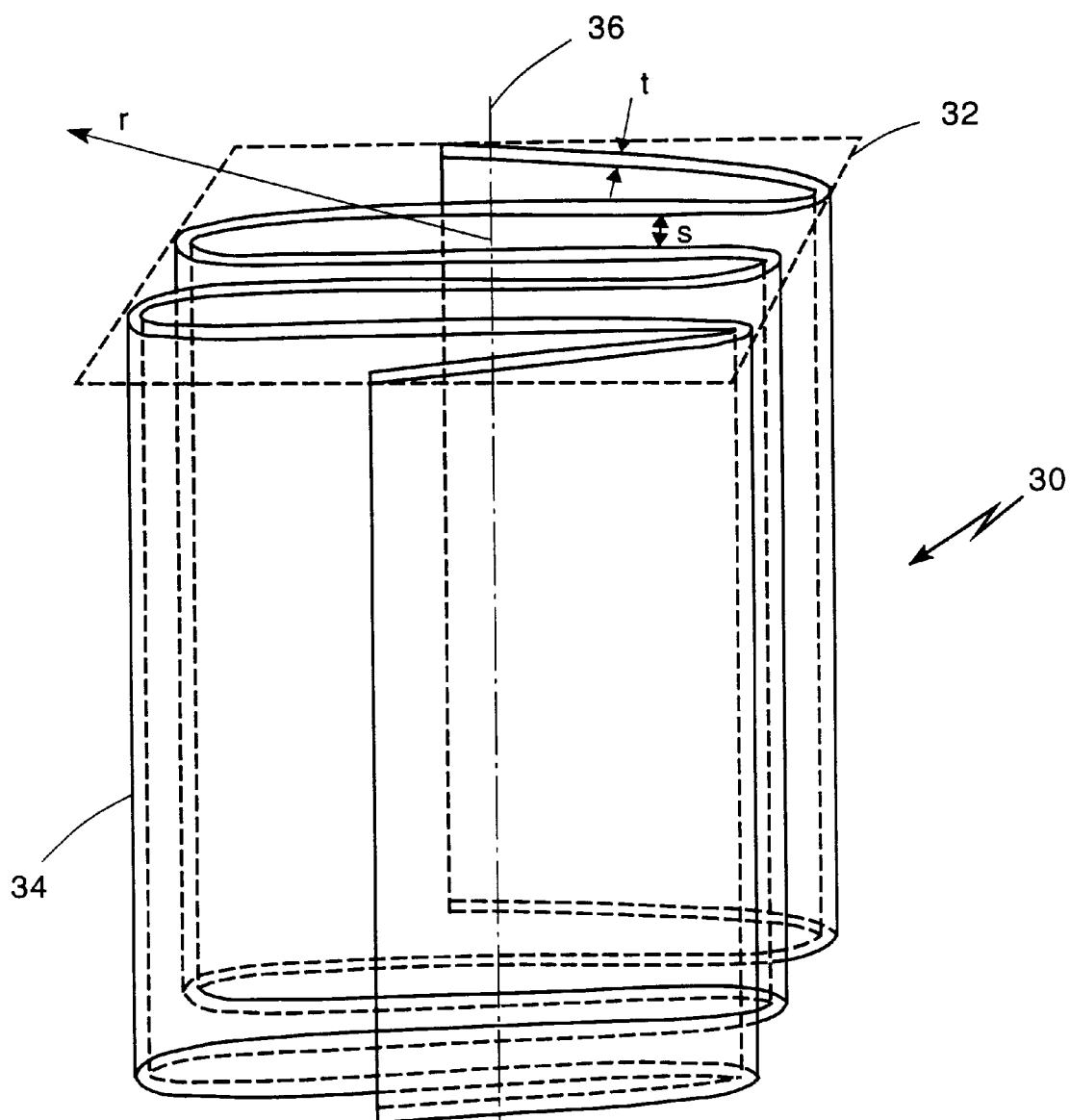
FIG. 3 is a perspective view of a sinusoidally folded implant having a general shape of a parallelepiped, shown partially in dash lines.

FIGS. 1, 2 and 3 show three implants of this invention. Each of the implants is either expandable (i.e., having a volume expansion rate of at least about 2 cm$^3$/cm$^3$) or unexpandable (i.e., no expansion beyond the expansion due to the inherent expanding property of the biopolymeric material of which it is made).

Shown in FIG. 1 is a generally cylindrically shaped implant 10. Implant 10 is formed from a spirally rolled porous matrix sheet 12. Matrix sheet 12 has a thickness, t, ranging from about 0.1 mm to about 3 mm (preferably, about 0.15 mm to about 0.3 mm), a density ranging from about 0.05 g/cm$^3$ to about 1.3 g/cm$^3$, and a pore size ranging from about 0.1 μm to about 1,500 μm, in which the pore size is defined as the longest distance of an elongated pore. Overlapping portions of rolled matrix sheet 12 define a spacing, s, that ranges from about 0.1 μm to about 2,000 μm.

Referring to FIGS. 2 and 3, implants of alternative configurations are illustrated. In FIG. 2, an implant 20 having a generally cylindrical shape, as indicated by a dashed circle 22, is shown in which a matrix sheet 24 has been sinusoidally folded to form the desired shape. With reference to FIG. 3, a matrix sheet 34 is sinusoidally folded so that an implant 30 has a general shape of a parallelepiped, as indicated by a dashed rectangle 32. The density, pore size, spacing s, and thickness t of the respective matrix sheets of implants 20 and 30 are the same as those discussed above for implant 10 (FIG. 1).

Implants having other configurations (not shown) are also possible. The matrix sheet can be folded into various patterns such that overlapping portions of the matrix sheet result in an implant with a compact geometry. For example, a matrix sheet can be folded to form an implant having a general shape of a "wrinkled" sheet of paper.

In one application, the implant is delivered by a delivery device to a void created by excised tissue taken as part of a surgical operation, for example, a biopsy of an organ or an interventional procedure such as catheterization. In another application, the implant is delivered near the external surface a body fluid vessel such as the urinary tract for treatment of incontinence.

If desired, the implant can be expandable. After an expandable implant has been placed in the body, it expands, upon absorption of a body fluid, to a volume with a volume expansion rate ranging from about 2 cm$^3$/cm$^3$ to about 100 cm$^3$/cm$^3$ (preferably, from about 4 cm$^3$/cm$^3$ to about 80 cm$^3$/cm$^3$). Upon expansion, the implant has a density ranging from about 0.01 g/cm$^3$ to about 0.50 g/cm$^3$, and a pore size ranging from about 10 $\mu$m to about 2,000 $\mu$m. Referring back to FIGS. 1, 2 and 3, once the implant has achieved an expanded state, spacing, s, between overlapping portions of matrix sheet 12 (or 24 or 34) ranges from about 100 $\mu$m to about 5000 $\mu$m.

An expandable implant expands in a geometrically and directionally controlled manner to a predetermined shape, size, and volume for optimal function in vivo. For instance, implant 10 (FIG. 1) may expand longitudinally along an axis 14, radially outward in all directions, r, extending from and perpendicular to axis 14, or both radially and longitudinally. Similarly, implants 20 and 30 (FIGS. 2 and 3) may expand longitudinally along their respective axes, 26 and 36, or radially, where again the radial direction is defined for implants 20 and 30 as all directions extending from and perpendicular to axes 26 and 36, respectively.

The expansion of an implant matrix enhances in vivo wound healing and tissue regeneration. For example, the implants will be useful as an adjunct in liver or kidney biopsy applications. The biopsy creates a wound void which can often result in bleeding complications. The expanded implant matrix will not only stop the bleeding via intrinsic hemostatic properties of the material of the implant (if such a material, e.g., collagen, is used to prepare the implant), but the channel openings created by overlapping portions of the rolled or folded matrix sheet and the additional surface area developed from such an expansion, will greatly facilitate the cellular ingrowth through the channel openings and cellular adhesion to the matrix surfaces. Similarly, the expandable implant can be used to stop the bleeding and facilitate the wound healing of percutaneously related wounds. Indeed, the expandable implant can be used in all wound healing applications which require the use of a wound healing material or template for tissue repair and regeneration. In treatments for urinary incontinence, where the intrinsic sphincter of the bladder neck is deficient causing urine leakage, the expandable implant having the longitudinal expansion capability described above offers a beneficial solution. In a longitudinally expanded state, the axis of the implant (e.g, axis 14 of implant 10) is positioned parallel to the direction of urine flow such that coaptation of the bladder neck is achieved.

To make implant 10, 20 or 30, a freeze-dried biopolymeric sheet matrix, which is biocompatible and bioresorbable, is first prepared in the manner described in detail below.

A number of biological materials can be used for preparing the sheet matrix. Among the suitable biological materials, type I collagen is preferred due to the availability of this material in large quantity, the ease of its isolation and purification, and proven biocompatible properties. Other fibril forming collagen such as types II, III, V and XI may be used either singularly or in combination with type I collagen for the manufacture of the matrix. The primary source of type I collagen is tendon, skin, bone, and ligament. Human or animal tissues may be used to isolate the collagen. The collagen produced from bioengineering methods such as from recombinant DNA may also be used. In general, animal tissues are preferred due to easy availability in fresh forms from local slaughter houses.

As an example, in preparing the sheet matrix, type I collagen is first isolated and purified. A review of the preparation of collagen can be found in "Methods in Enzymology," vol. 82, pp. 33–64, 1982 and from "The Preparation of Highly Purified Insoluble Collagen, Oneson, I, et al. J. Am. Leather Chemists Asso., Vol. LXV, page 440–450, 1970". In particular, the procedure for the purification of type I collagen of the present invention is described in an example below.

A collagen dispersion is then prepared. One such preparation is taught in U.S. Pat. No. 3,157,524, and another in U.S. Pat. No. 3,520,402. In particular, the collagen dispersion can be prepared according to methods described in two actual examples provided below.

If the implant matrix is intended to function as a delivery vehicle for bioactive molecules, then in addition to type I collagen, bioactive molecules may optionally be included in the dispersion, such as antibiotics, thrombin, polysaccharide (e.g., hyaluronic acid, chondroitin sulfates, alginic acids, chitosan, and the like), growth factors (e.g., epidermal growth factors, transforming growth factor β, and the like), glycoproteins (e.g., fibronectin, laminin, and the like), various types of collagen, polynucleotide, or a combination thereof.

Subsequently, the collagen dispersion is poured into a freeze-dry tray. The depth of the dispersion in the tray is generally about 0.5 to 10 mm, preferably from 1 to 5 mm, most preferably from 1.5 to 3.5 mm. The tray containing the dispersion is then placed in a freezer maintained at a temperature of from about −10° C. to about −50° C. for a length of time sufficient to freeze the water present in the dispersion, generally for about 1 to about 24 hours. The frozen dispersion is then subjected to freeze-drying so as to remove the frozen water. This freeze-drying procedure is carried out in a commercial freeze dryer, such as that manufactured by Virtis, Stokes or Hull, at conditions well known to those skilled in the art. Typically, the vacuum within the drying chamber is maintained at from about 50 $\mu$m to about 300 $\mu$m of Hg, at a temperature of from about −10° C. to about −50° C. for about 16 to about 96 hours. The temperature is then raised to about 25° C. for about 3 to 24 hours. The pore size can be controlled by varying the density of the matrix and by controlling the speed of freezing of the matrix prior to freeze-drying, and is determined from scanning electron micrographs.

Depending on the particular application, implant 10 can be formed from the freeze-dried biopolymeric sheet matrix thus obtained cut to a specified size. The cut matrix sheet is spirally rolled and then inserted into a crosslinking housing, which is a porous cylinder having an internal diameter equivalent to the diameter of the rolled matrix sheet. The rolled matrix is subjected to a crosslinking process which introduces intermolecular crosslinks to stabilize the matrix sheet so that it remains in the form of a cylinder. Crosslinking after pre-forming the spiral shape is important as it locks in the spiral shape such that a mechanical distortion to the implant will only result in a temporary shape or size change induced by the imposed force. Upon removal of the imposed force, the original shape of the implant will be restored. The restoration is particularly prominent when the implant is placed in an aqueous environment.

Alternatively, the spiral geometry of implant 10 can be pre-formed in a spiral mold. In this case, a dispersion of a selected biopolymeric material is poured into the spiral mold. The dispersion in the mold is then subjected to a freeze-drying process thereby pre-forming a spirally shaped implant without physically rolling the matrix sheet. The pre-formed implant is subsequently subjected to the crosslinking process described above. A spirally rolled matrix can also be created from a solid matrix by either carving a spiral geometry in the solid matrix or cutting the matrix with a spiral die.

The crosslinking is carried out by means well known in the art. Any reagents which can chemically react with the amino group of lysine or hydroxylysine, the hydroxyl group of serine, threonine or tyrosine, the guanidino group of arginine, the carboxyl group of glutamic or aspartic acid, and the imidazo group of histidine that can link the side chains of different collagen molecules may be used to crosslink the matrix. This can be accomplished with chromium sulfate, formaldehyde, glutaraldehyde, carbodiimide, adipyl chloride, hexamethylene diisocyanate, dye mediated photooxidation, monosaccharide, and the like. The crosslinks introduced via heat and vacuum known in the art as dehydrothermal crosslinking may also be used.

The stability of the crosslinked matrix in vivo is dependent upon the degree of intermolecular crosslinking in the collagen matrix. Factors controlling the extent of crosslinking are the type and concentration of the crosslinking agent; the pH, time and the temperature of incubation in the liquid phase; or the vapor pressure of the crosslinking agent, time, temperature and the relative humidity when carrying out crosslinking in the vapor phase. Desirably, the collagen matrix of the present invention is crosslinked to the extent that the collagen is completely resorbed within about 4 to about 52 weeks.

The crosslinking of the freeze-dried, spiral formed matrix defines the spiral shape of the matrix and upon mechanical distortion, the matrix restores its spiral configuration when hydrated.

The extent of crosslinking of the collagen matrix of the present invention can be monitored by the hydrothermal shrinkage temperature ($T_s$) of the matrix, i.e. the onset temperature at which the matrix begins to shrink in its dimension in an aqueous environment as a result of the unwinding of the triple helical structure of the collagen molecules. The methods for measuring the shrinkage temperature of a material is well known in the art, such as by a differential scanning calorimeter, or by measuring the dimensional change using a cathetometer. Generally, the degree of crosslinking is such that the shrinkage temperature of the collagen matrix is in the range of from about 50° C. to about 80° C., preferably from about 55° C. to about 65° C.

As an example, the collagen matrix can be crosslinked with formaldehyde vapor. Either commercial formaldehyde vapor or vapor of formaldehyde generated from a formaldehyde solution may be used. Particularly, the crosslinking is conducted in a chamber with a relative humidity in the range of from about 80% to about 100%, and in the presence of an excess amount of formaldehyde vapor, at a temperature of about 25° C. for a period from about 30 minutes to about 8 hours.

The crosslinked collagen matrix is then subjected to a water vapor treatment. The water vapor may be generated from any commercial humidifier or simply by water vapor generated in a closed system at a given temperature. As a result of this water treatment, the collagen matrix has a water uptake of about 10 to 50% by weight, based on the weight of the dry material.

Further compression of the water vapor-treated matrix can be performed to reduce its size and increase its density, thereby producing an expandable implant matrix. The compression can be accomplished with a plastic or a stainless steel roller that rolls over the spiral sheet while compressing the sheet into a thinner membrane. Typically, the thickness of the spiral sheet is about 3 mm before compression, while the compressed sheet will have a thickness that ranges from about 0.1 mm to about 0.3 mm. The spacing between overlapping portions of the compressed spiral matrix sheet will be larger than the spacing prior to compression due to the reduction of the thickness of the spiral sheet. It is often desirable to re-roll the compressed spiral matrix to a more compact geometry before inserting it into a delivery vehicle. The spirally compressed matrix thus obtained is radially expandable. It can also be further subjected to an additional compression along the longitudinal axis to produce an implant that will also expand longitudinally as discussed above.

The order of the production process of compression and crosslinking can be reversed. For example, a freeze-dried sheet is first compressed to a thin membrane, spirally rolled, and then subjected to the crosslinking process. The volume of such an implant will not increase significantly upon absorption of a fluid. One medical application for this type of implants is in the area of tubular vascular tissue repair. For example, one can unroll such an implant so as to wrap it around a damaged or repaired vessel (e.g., the suture lines of an end-to-end bypass procedure) to exclude fibrous tissue ingrowth into the repair sites. As another example, a version of this type of implants, i.e., one that has a tubular shape with a wall formed of a matrix sheet having overlapping portions, can be delivered to the inside of a damaged vessel to facilitate wound healing.

Implants 20 and 30, as well as others within the scope of this invention, can be prepared in a manner analogous to what is described above.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever. All publications, including U.S. patents, cited herein are incorporated by reference.

Preparation of Purified Collagen Fibers

The fat and fascia of the calf flexor tendon was carefully cleaned and removed and washed with water. The cleaned tendon was frozen and diminuted by slicing into 0.5 mm slices with a meat slicer. The tendon was extracted with 5 volumes of distilled water for 24 hours with one change of water. The water-extracted tendon was then extracted in 0.2 M HCl for 24 hours in the presence of 1 M $Na_2SO_4$ at 25° C. with constant agitation. The acid was decanted and the tendon was then extracted in 0.75 M NaOH for 24 hours in the presence of 1 M $Na_2SO_4$ at 25° C. The alkaline solution was decanted and the tendon was neutralized with 0.05 M HCl. After neutralization, the tendon collagen was extensively washed with distilled water. The tendon collagen was then extracted in 5 volumes of isopropanol at 25° C. for 24 hours with two change of equal volume of isopropanol. The purified collagen fibers were air dried and stored dry at room temperature.

Preparation of Collagen Dispersion via Alkaline Swelling

An aliquot of the purified collagen fibers thus obtained was first suspended in $1 \times 10^{-3}$ M NaOH solution. The amount of fibers and base solution used was such that a 1.0% (w/v) of collagen suspension was reached. The swollen fibers were then homogenized in a Silverson homogenizer (East Longmeadow, Mass.) for 120 seconds. The dispersed collagen material was filtered through a 100 μm stainless steel mesh. The pH of the dispersion was then slowly adjusted to about 7.0 by adding 0.01 M HCl. The dispersed material was de-aired by centrifugation at 3,000 g for 30 min. and the supernatant was decanted. The final concentration of collagen in the dispersion was 1.5% (w/v).

Preparation of Collagen Dispersion via Fiber Coacervation

Alternatively, an aliquot of the purified collagen fibers was first suspended in 0.07 M Lactic acid solution. The amount of fibers and acid solution used was such that a 0.7% (w/v) of collagen suspension was reached. The swollen fibers were then homogenized in Silverson homogenizer for 60 seconds. The dispersed collagen material was filtered through a 40 μm stainless steel mesh. The dispersed material was then de-aired by vacuum. The dispersed, de-aired material was then coacervated by adding 0.3% $NH_4OH$ to pH 4.5–5.0. The coacervated fibers were removed for further processing.

Preparation of a Folded Collagen Matrix with Expansion Property

Collagen dispersion or coacervated collagen fibers thus obtained was poured into a stainless steel tray to a depth of 2 mm. The collagen containing tray was then subjected to a freeze-drying procedure using a Virtis commercial freeze dryer. The conditions for freeze-drying were: freeze at −40° C. for 6–16 hours, drying at 150 μm Hg at −10° C. for 48 hours followed by drying at 25° C. for 8–16 hours. The freeze-dried collagen matrix was cut into 1.5 cm×3 cm sheet, folded by repeated sinusoidal foldings into a multi-layered configuration, inserted into a porous cylinder, and subjected to a formaldehyde vapor crosslinking in a crosslinking chamber containing an excess amount of formaldehyde vapor (generated by a 2% formaldehyde solution at 25° C.), 95% relative humidity at 25° C. for 120 minutes. The crosslinked collagen matrix was humidified with water vapor generated at 25° C. for 4–8 hours in a closed chamber. The water vapor treated matrix was then compressed using a plastic cylinder so as to produce a membrane from original 2 mm to about 0.2 mm in thickness. The compressed membrane was re-folded into a dense multi-layered configuration with an overall width of about 2 mm. The matrix was then inserted into a pre-fabricated delivery means.

Preparation of a Rolled Collagen Matrix with Expansion Property

Collagen dispersion or coacervated collagen fibers were poured into a stainless steel tray to a depth of 2 mm. The collagen containing tray was then subjected to a freeze-drying procedure using a Virtis commercial freeze dryer. The conditions for freeze-drying were: freeze at −40° C. for 6–16 hours, drying at 150 μm Hg at −10° C. for 48 hours followed by drying at 25° C. for 8–16 hours. The freeze-dried collagen matrix was cut into 1.5 cm×3 cm sheet, rolled into a spiral configuration, inserted into a porous cylinder and subjected to a formaldehyde vapor crosslinking in a crosslinking chamber containing an excess amount of formaldehyde vapor (generated by a 2% formaldehyde solution at 25° C.), 95% relative humidity at 25° C. for 120 minutes. The crosslinked collagen matrix was humidified with water vapor generated at 25° C. for 4–8 hours in a closed chamber. The water vapor treated matrix was then compressed using a plastic cylinder so as to produce a spiral membrane from original 2 mm to about 0.2 mm in thickness. The compressed spiral membrane was re-rolled into a dense matrix with an overall width of about 2 mm, and then inserted into a pre-fabricated delivery means.

Alteratively, collagen dispersion or coacervated collagen fibers were poured into a stainless steel tray to a depth of 2 mm. The collagen containing tray was then subjected to a freeze-drying procedure using a Virtis commercial freeze dryer. The conditions for freeze-drying were: freeze at −40° C. for 6–16 hours, drying at 150 μm Hg at −10° C. for 48 hours followed by drying at 25° C. for 8–16 hours. The freeze-dried collagen matrix was cut into 1.5 cm×3 cm sheet. The freeze-dried matrix was humidified with water vapor generated at 25° C. for 4–8 hours in a closed chamber. The sheet was compressed with a plastic cylinder to a 0.2 mm thick membrane. The membrane was rolled into a spiral configuration, inserted into a porous cylinder and subjected to a formaldehyde vapor crosslinking in a crosslinking chamber containing an excess amount of formaldehyde vapor (generated by a 2% formaldehyde solution at 25° C.), 95% relative humidity at 25° C. for 120 minutes. The crosslinked spiral membrane was re-rolled into a dense matrix with an overall width of about 2 mm, and then inserted into a pre-fabricated delivery means.

Preparation of a Collagen Matrix with Spiral and Longitudinal Expansion Properties Collagen dispersion or coacervated collagen fibers were poured into a stainless steel tray to a depth of 2 mm. The collagen containing tray was then subjected to a freeze-drying procedure using a Virtis commercial freeze dryer. The conditions for freeze-drying were: freeze at −40° C. for 6–16 hours, drying at 150 μm Hg at −10° C. for 48 hours followed by drying at 25° C. for 8–16 hours. The freeze-dried collagen matrix was cut into 1.5 cm×3 cm sheet, rolled into a spiral configuration, inserted into a porous cylindrical tube and subjected to a formaldehyde vapor crosslinking in a crosslinking chamber containing an excess amount of formaldehyde vapor (generated by a 2% formaldehyde solution at 25° C.), 95% relative humidity at 25° C. for 120 minutes. The crosslinked collagen matrix was humidified with water vapor generated at 25° C. for 4–8 hours in a closed chamber. The water vapor treated matrix was first compressed using a plastic cylinder so as to produce a spiral membrane from 2 mm to about 0.2 mm in thickness. The compressed spiral membrane was re-rolled into a dense matrix with an overall width of about 2 mm. The spirally compressed matrix was then inserted into a stainless steel cylindrical tube of about 2 mm in inner diameter and subjected to a compression along the longitudinal direction so as to reduce the length to about 3 mm–5 mm. The spiral matrix was then inserted into a pre-fabricated delivery means.

Method of Using a Spirally Expanding Collagen Matrix in a Percutaneous Wound

An appropriately sized spiral expanding collagen implant is inserted into a tubular delivery system for delivery to a puncture site. The collagen implant is deposited at the puncture site and allowed to absorb the body fluid and expand spirally. The delivery system is then removed.

Method of Using a Spirally Expanding Matrix to Stop Bleeding and Facilitate Wound Healing of a Soft Tissue Site Post Tissue Biopsy After a liver or kidney biopsy has been conducted, an appropriately sized delivery means containing a spirally expanding collagen implant is inserted via a biopsy needle sheath through a percutaneous site. The collagen implant is then pushed out of the tubular delivery means via a piston to the tissue site while the delivery means and the biopsy needle sheath are slowly withdrawn. The collagen implant expands spirally to fill the void of the soft tissue biopsy site.

Method of Using a Spirally and Longitudinally Expanding Matrix to Increase an In Vivo Volume of a Soft Tissue Site An appropriately sized delivery means containing a spirally and longitudinally expanding collagen implant is inserted into the bladder neck site. The implant is then released out of the delivery means and deposited at the tissue site while the delivery means is slowly being withdrawn. The implant expanded spirally and longitudinally to increase the volume at the sphincter site and cause coaptation of the sphincter tissue.

Method of Using a Spirally Expanding Matrix to Stop Bleeding and Facilitate Wound Healing of a Soft Tissue Site Post Surgery An appropriately sized delivery means containing a spirally expanding collagen implant is inserted into the tissue site post surgery via a delivery device. The collagen implant is then pushed out of the delivery means via a piston to the tissue site while the delivery means is slowly withdrawn. The collagen implant expands spirally to fill the void of the soft tissue wound site.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims. For example, any solid implant matrix that is generally shaped as a cylinder or as a parallelepiped and has longitudinal holes (e.g., produced by drilling) to facilitate cellular ingrowth is within the spirit of this invention.

What is claimed is:

1. An implant comprising a porous matrix sheet made of biocompatible and bioresorbable biopolymeric material, said matrix sheet having at least one portion spaced from and overlapping another portion of said matrix sheet; wherein said implant having a density ranging from about 0.05 g/cm$^3$ to about 1.3 g/cm$^3$, a pore size ranging from about 0.1 µm to about 1,500 µm, and a spacing between overlapping portions of said matrix sheet ranging from about 0.1 µm to about 2,000 µm, and, upon absorption of a fluid, is expandable geometrically and directionally and has a volume expansion rate ranging from about 2 cm$^3$/cm$^3$ to about 100 cm$^3$/cm$^3$, and, in the expanded state, has a density ranging from about 0.01 g/cm$^3$ to about 0.5 g/cm$^3$, a pore size ranging from about 10 µm to about 2,000 µm, and a spacing between overlapping portions of said matrix sheet ranging from about 10 µm to about 5,000 µm.

2. The implant of claim 1, wherein said implant, upon absorption of a fluid, is expandable having a volume expansion rate ranging from about 4 cm$^3$/cm$^3$ to about 80 cm$^3$/cm$^3$.

3. The implant of claim 2, wherein said implant is radially expandable upon absorption of a fluid.

4. The implant of claim 2, wherein said implant is longitudinally expandable upon absorption of a fluid.

5. The implant of claim 4, wherein said implant is radially expandable upon absorption of a fluid.

6. The implant of claim 1, wherein said matrix sheet is spirally rolled so that said implant has a generally cylindrical shape.

7. The implant of claim 6, wherein said implant, upon absorption of a fluid, is expandable having a volume expansion rate ranging from about 4 cm$^3$/cm$^3$ to about 80 cm$^3$/cm$^3$.

8. The implant of claim 7, wherein said implant is radially expandable upon absorption of a fluid.

9. The implant of claim 7, wherein said implant is longitudinally expandable upon absorption of a fluid.

10. The implant of claim 9, wherein said implant is radially expandable upon absorption of a fluid.

11. The implant of claim 1, wherein said matrix sheet is sinusoidally folded so that said implant is generally shaped as a cylinder or as a parallelepiped.

12. The implant of claim 11, wherein said implant, upon absorption of a fluid, is expandable having a volume expansion rate ranging from about 4 cm$^3$/cm$^3$ to about 80 cm$^3$/cm$^3$.

13. The implant of claim 12, wherein said implant is radially expandable upon absorption of a fluid.

14. The implant of claim 12, wherein said implant is longitudinally expandable upon absorption of a fluid.

15. The implant of claim 14, wherein said implant is radially expandable upon absorption of a fluid.

16. The implant of claim 6, wherein said biopolymeric material is collagen.

17. The implant of claim 16, wherein said implant, upon absorption of a fluid, is expandable having a volume expansion rate ranging from about 4 cm$^3$/cm$^3$ to about 80 cm$^3$/cm$^3$.

18. The implant of claim 17, wherein said implant is radially expandable upon absorption of a fluid.

19. The implant of claim 17, wherein said implant is longitudinally expandable upon absorption of a fluid.

20. The implant of claim 19, wherein said implant is radially expandable upon absorption of a fluid.

21. The implant of claim 11, wherein said biopolymeric material is collagen.

22. The implant of claim 21, wherein said implant, upon absorption of a fluid, is expandable having a volume expansion rate ranging from about 4 cm$^3$/cm$^3$ to about 80 cm$^3$/cm$^3$.

23. The implant of claim 22, wherein said implant is radially expandable upon absorption of a fluid.

24. The implant of claim 22, wherein said implant is longitudinally expandable upon absorption of a fluid.

25. The implant of claim 24, wherein said implant is radially expandable upon absorption of a fluid.

26. The implant of claim 1, wherein said biopolymeric material is collagen.

* * * * *